United States Patent [19]
von Alfthan et al.

[11] Patent Number: 5,048,325
[45] Date of Patent: Sep. 17, 1991

[54] MEASURING CELL

[75] Inventors: Georg C. von Alfthan, Kauniainen; Antti I. Ahonen, Helsinki, both of Finland

[73] Assignee: Outokumpu Oy, Helsinki, Finland

[21] Appl. No.: 627,541

[22] Filed: Dec. 7, 1990

Related U.S. Application Data

[63] Continuation of Ser. No. 393,543, Aug. 11, 1989, abandoned.

[30] Foreign Application Priority Data

Aug. 12, 1988 [FI] Finland .................................. 883743

[51] Int. Cl.$^5$ .............................................. G01N 21/05
[52] U.S. Cl. ...................................... 73/61 R; 356/441
[58] Field of Search ........... 73/61.1 R, 863.52, 863.42, 73/863.41, 61 R; 378/47; 250/435, 437, 438; 356/441, 442

[56] References Cited

U.S. PATENT DOCUMENTS

| | | | |
|---|---|---|---|
| 3,354,308 | 11/1967 | Engel et al. | 378/47 |
| 3,749,910 | 7/1973 | Carr-Brion et al. | 378/86 |
| 3,980,882 | 9/1976 | Carr-Brion et al. | 378/47 |
| 4,126,226 | 11/1978 | Bello et al. | 378/47 X |
| 4,289,020 | 9/1981 | Paap | 73/61.1 R |
| 4,412,451 | 11/1983 | Uusitalo et al. | 73/61 R X |
| 4,492,868 | 1/1985 | Jelveztum et al. | 356/441 X |
| 4,509,360 | 4/1985 | Erwin et al. | 73/61 R |
| 4,916,719 | 4/1990 | Kawatra et al. | 378/47 X |

FOREIGN PATENT DOCUMENTS

| | | | |
|---|---|---|---|
| 1251547 | 10/1967 | Fed. Rep. of Germany | 73/61 R |
| 2433355 | 1/1976 | Fed. Rep. of Germany | 356/442 |
| 2445148 | 4/1976 | Fed. Rep. of Germany | 73/61 R |
| 48678 | 3/1982 | Japan | 250/437 |
| 165141 | 7/1987 | Japan | 73/61 R |
| 121729 | 5/1988 | Japan | 73/61 R |
| 8801737 | 3/1988 | PCT Int'l Appl. | 356/442 |
| 534355 | 4/1973 | Switzerland | 356/442 |
| 581835 | 11/1976 | Switzerland | 73/61.1 R |
| 192432 | 3/1967 | U.S.S.R. | 356/442 |
| 1109276 | 4/1968 | United Kingdom | 378/47 |
| 1400587 | 7/1975 | United Kingdom | 378/47 |

OTHER PUBLICATIONS

"Multicomponent On-Stream Analyzers for Process Monitoring and Control"; *Intech*; Jul. 1979 pp. 38–44; by John Jutila.

*Primary Examiner*—Tom Noland
*Attorney, Agent, or Firm*—Dellett, Smith-Hill and Bedell

[57] ABSTRACT

The invention relates to a measuring cell (1) designed for measuring the contents of the components present in slurries which are in a flowing motion, the measuring cell comprising an inlet pipe (2) and an outlet pipe (9) for the slurry and a measuring window (3). According to the invention, the inlet pipe (2) is placed at a given distance from and in an inclined position with respect to the plane contained in the measuring window (3), in order to direct the slurry jet entering from the inlet pipe (2) to a point that is approximately one internal radius of the inlet passage (2) in front of the center of the measuring window (3).

12 Claims, 1 Drawing Sheet

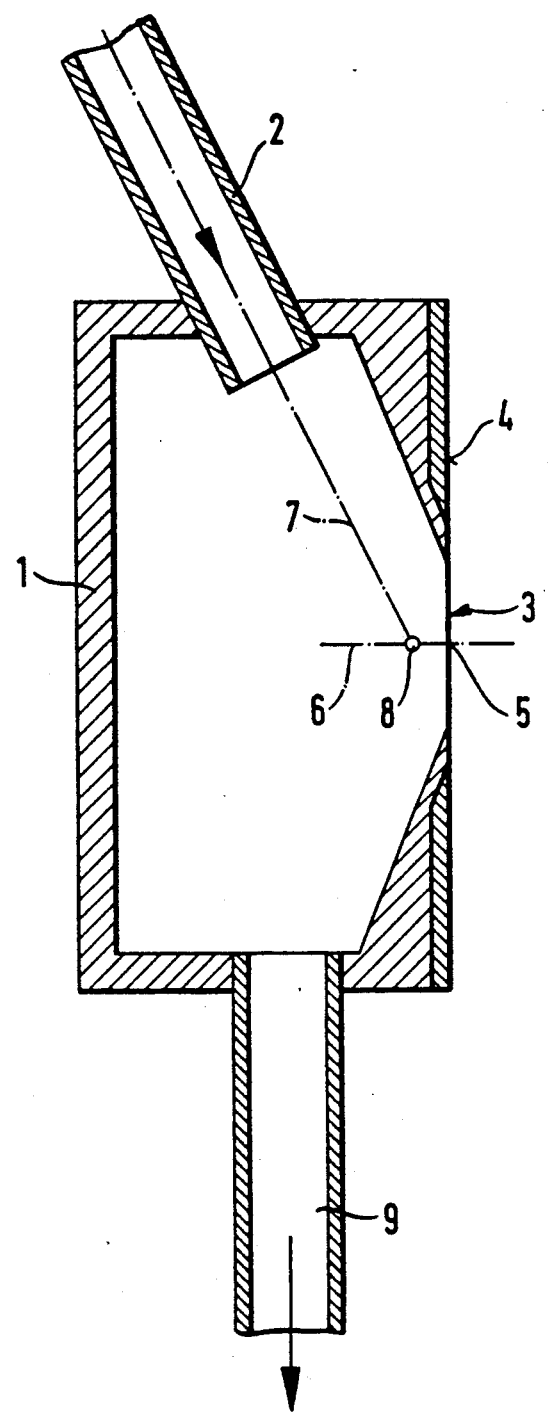

MEASURING CELL

This is a continuation of application Ser. No. 07/393,543 filed Aug. 11, 1989 and now abandoned.

BACKGROUND OF THE INVENTION

The present invention relates to a measuring cell for measuring the contents of components present in slurries.

Generally the measuring of components present in a slurry is carried out by means of a measuring cell, where the slurry is conducted, via an inlet pipe, to a measuring chamber provided with a measuring window, and then conducted out via an outlet pipe. In the measuring chamber provided with a window, the slurry is subjected for instance to X-ray radiation in order to create the intensities caused by the various components contained in the slurry. In the previously known measuring cells, the slurry is generally conducted through the measuring chamber provided with a window so that the slurry is turbulent within the cell. When a rapid flow has been necessary in order to create turbulence, the flow has sometimes been conducted to pass by the measuring window, in which case the wearing of the window is great. Smaller velocities have also been used in the vicinity of the window, in which case the solid particles contained in the slurry have not given a reliable representation of the sample flow, which in part makes it more difficult to determine the contents of the various components. Measuring cells where the slurry is conducted into the measuring chamber through the side, so that the slurry flows directly towards the measuring window, have also been tried in the prior art. However, it has turned out that such a flow wears the measuring window a great deal, wherefore the same window cannot be used for a longer period of time.

SUMMARY OF THE INVENTION

The object of the present invention is to eliminate some of the drawbacks of the prior art and to achieve an improved measuring cell suitable for measuring the contents of components contained in slurries, wherein the slurry enters, via the inlet pipe of the measuring cell, at an essentially high speed to a relatively large space in the measuring cell, thus causing a strong turbulence by the measuring window at an essentially low speed.

According to the invention, the inlet pipe of the slurry entering the measuring cell is placed in an inclined position with respect to the measuring window located in the measuring cell, so that the slurry jet sprayed from the inlet pipe at least partly hits the measuring window in a slanted direction at a distance where the jet speed has become essentially totally turbulent, and which distance is dependent on the diameter of the inlet pipe. By means of the turbulence there is created a slurry sample to be measured in a known fashion, which gives an essentially good representation of the slurry flow under measurement.

DESCRIPTION OF THE DRAWING

In the following, the invention is explained in more detail with reference to the appended drawing, which is an illustration of a preferred embodiment of the invention, seen from the side in partial cross-section.

DETAILED DESCRIPTION

According to the drawing, the slurry flow under treatment enters the measuring cell 1 via the inlet pipe 2 and is discharged via the outlet pipe 9. The inlet pipe 2 is placed in an inclined position so that the inlet pipe 2 forms, together with the plane 4 contained by the measuring window 3 located in the measuring cell, an angle of 10-45°, preferably 30-40°. The perpendicular axis 6 of the measuring window, passing through the center point 5 of the measuring window, and the axis of symmetry 7 of the inlet pipe, intersect at the point 8. The distance between the intersection point 8 and the measuring window 3 is dependent on the diameter of the inlet pipe, and is advantageously about half of the diameter of the inlet pipe 2. Similarly, the distance between the inlet pipe 2 and the point 8 is dependent on the diameter of the inlet pipe, and must be 3-7 times, preferably 4-6 times the diameter of the inlet pipe, so that the slurry jet discharged from the inlet pipe 2 is made essentially turbulent in the measuring cell 1 before the jet reaches the measuring window 3.

Another factor affecting the creation of turbulence is the average flow speed of the slurry jet, sprayed from the inlet pipe 2, in the cross-sectional area of the measuring cell 1. In order to make the average flow speed of the slurry jet favourable to the creation of turbulence, the cross-sectional area of the measuring cell 1 must be at least 5, times the diameter of the inlet pipe, when the cross-sectional area of the measuring cell 1 is measured with respect to the center point 5 of the measuring window.

By directing, according to the method of the present invention, the slurry flow to be treated in the measuring cell in a slanted position towards the measuring window, the wearing of the measuring window can be essentially reduced in comparison with a perpendicular jet.

We claim:

1. A measuring cell for determining the composition of a flowing slurry, the measuring cell comprising:
    means defining an inlet passage, the inlet passage having a central axis;
    means defining an outlet passage; and
    a substantially planar measuring window having a center point, the measuring window being disposed with its plane inclined relative to the central axis of the inlet passage and so that an axis through the center point of the measuring window and perpendicular to the plane of the measuring window approximately intersects the central axis of the inlet passage at a point internal to the measuring cell and spaced apart from the measuring window, whereby slurry entering the measuring cell along said central axis is directed toward the measuring window.

2. A measuring cell according to claim 1, wherein the inlet passage is circular in cross section and the distance between said point and the measuring window is approximately equal to one half of the diameter of the inlet passage.

3. A measuring cell according to claim 1, wherein the inlet passage is circular in cross section and the distance between said point and the inlet passage is three to seven times the diameter of the inlet passage.

4. A measuring cell according to claim 3, wherein the distance between said point and the inlet passage is four to six times the diameter of the inlet passage.

5. A measuring cell according to claim 1, wherein the central axis of the inlet passage intersects the plane of the measuring window at an angle of from 10-45 degrees.

6. A measuring cell according to claim 1, wherein the central axis of the inlet passage intersects the plane of the measuring window at an angle of from 30-40 degrees.

7. A measuring cell for determining the composition of a flowing slurry, the measuring cell comprising:
   wall means enclosing a measurement volume for receiving a flow of slurry, the wall means defining an inlet passage, an outlet passage, and an opening, the inlet passage having a central axis; and
   a substantially planar measuring window occluding the opening and having a center point, the opening being disposed with its plane inclined relative to the central axis of the inlet passage and so that an axis through the center point of the measuring window and perpendicular to the plane of the measuring window approximately intersects the central axis of the inlet passage at a point internal to the measuring cell and spaced apart from the measuring window, whereby slurry entering the measuring cell along said central axis is directed toward the measuring window.

8. A measuring cell according to claim 7, wherein the inlet passage is circular in cross section and the distance between said point and the measuring window is approximately equal to one half of the diameter of the inlet passage.

9. A measuring cell according to claim 7, wherein the inlet passage is circular in cross section and the distance between said point and the inlet passage is three to seven times the diameter of the inlet passage.

10. A measuring cell according to claim 9, wherein the distance between said point and the inlet passage is four to six times the diameter of the inlet passage.

11. A measuring cell according to claim 7, wherein the central axis of the inlet passage intersects the plane of the measuring window at an angle of from 10-45 degrees.

12. A measuring cell according to claim 7, wherein the central axis of the inlet passage intersects the plane of the measuring window at an angle of from 30-40 degrees.

* * * * *